(12) United States Patent
Patton et al.

(10) Patent No.: US 8,436,110 B2
(45) Date of Patent: May 7, 2013

(54) OLEFIN METATHESIS PROCESS EMPLOYING BIMETALLIC RUTHENIUM COMPLEX WITH BRIDGING HYDRIDO LIGANDS

(75) Inventors: Jasson T. Patton, Midland, MI (US); Francis J. Timmers, Midland, MI (US)

(73) Assignee: Dow Global Technologies LLC

( * ) Notice: Subject to any disclaimer, the term of this patent is extended or adjusted under 35 U.S.C. 154(b) by 308 days.

(21) Appl. No.: 12/606,532

(22) Filed: Oct. 27, 2009

(65) Prior Publication Data

US 2010/0113719 A1  May 6, 2010

Related U.S. Application Data

(60) Provisional application No. 61/110,158, filed on Oct. 31, 2008.

(51) Int. Cl.
*C08F 4/06* (2006.01)
*C08F 4/00* (2006.01)

(52) U.S. Cl.
USPC ........................................................ 526/113

(58) Field of Classification Search ............... 526/113
See application file for complete search history.

(56) References Cited

U.S. PATENT DOCUMENTS

| | | | |
|---|---|---|---|
| 4,545,941 | A | 10/1985 | Rosenburg |
| 4,560,792 | A | 12/1985 | Banasiak |
| 4,698,451 | A | 10/1987 | Diefenbach |
| 4,704,377 | A | 11/1987 | Diefenbach |
| 4,772,758 | A | 9/1988 | Kaufhold |
| 4,943,397 | A | 7/1990 | Johnson |
| 5,143,885 | A | 9/1992 | Warwel et al. |
| 5,218,131 | A | 6/1993 | Warwel et al. |
| 5,312,940 | A | 5/1994 | Grubbs et al. |
| 5,342,985 | A | 8/1994 | Herrmann et al. |
| 5,352,812 | A | 10/1994 | Feldman et al. |
| 5,539,060 | A | 7/1996 | Tsunogae et al. |
| 5,932,664 | A | 8/1999 | Chen et al. |
| 6,060,572 | A | 5/2000 | Gillis et al. |
| 6,156,692 | A | 12/2000 | Nubel et al. |
| 6,197,894 | B1 | 3/2001 | Sunaga et al. |
| 6,552,139 | B1 | 4/2003 | Herrmann et al. |
| 6,635,768 | B1 | 10/2003 | Herrmann et al. |
| 6,800,170 | B2 | 10/2004 | Kendall et al. |
| 7,102,047 | B2 | 9/2006 | Grubbs et al. |
| 7,119,216 | B2 | 10/2006 | Newman et al. |
| 7,176,336 | B2 | 2/2007 | Maughon et al. |
| 7,576,227 | B2 | 8/2009 | Lysenko et al. |
| 2003/0149274 | A1 | 8/2003 | Herrmann et al. |
| 2007/0043188 | A1 | 2/2007 | Schaubroeck et al. |
| 2008/0103346 | A1* | 5/2008 | Burdett et al. .................. 585/818 |
| 2010/0010161 | A1 | 1/2010 | Arriola et al. |
| 2010/0069573 | A1 | 3/2010 | Arriola et al. |

FOREIGN PATENT DOCUMENTS

| | | |
|---|---|---|
| DE | 281594 | 8/1990 |
| DE | 4107056 | 9/1992 |
| DE | 10041345 | 3/2002 |
| EP | 0084437 | 7/1983 |
| EP | 0099572 | 2/1984 |
| EP | 0328230 | 8/1989 |
| EP | 1757613 | 2/2007 |
| JP | 56077243 | 6/1981 |
| JP | 03066725 | 3/1991 |
| WO | 9320111 | 10/1993 |
| WO | 9604289 | 2/1996 |
| WO | 9706185 | 2/1997 |
| WO | 9900397 | 1/1999 |
| WO | 9922866 | 5/1999 |
| WO | 0015339 | 3/2000 |
| WO | 0058322 | 10/2000 |
| WO | 0071554 | 11/2000 |
| WO | 02076920 | 10/2002 |
| WO | 03093215 | 11/2003 |
| WO | 2004037754 | 5/2004 |
| WO | 2005035121 | 4/2005 |
| WO | 2005040077 | 5/2005 |
| WO | 2008027267 | 3/2008 |
| WO | 2008027268 | 3/2008 |
| WO | 2008027269 | 3/2008 |
| WO | 2008027283 | 3/2008 |
| WO | 2009009158 | 1/2009 |

OTHER PUBLICATIONS

Tschan et al., Organometallics 2005, 24, 1974-1981.*
Ahmed et al., "A recyclable 'boomerang' polymer-supported ruthenium catalyst for olefin metathesis", Tetrahedron Letters, 1999, pp. 8657-8662, vol. 40, Elsevier Science Ltd.
Ahn et al., "A Convenient Method for the Efficient Removal of Ruthenium Byproducts Generated During Olefin Metathesis Reactions", Organic Letters, 2001, vol. 3 No. 9, pp. 1411-1413, American Chemical Society.
Akita et al., "Specific C-C coupling of the labile diruthenium bridging methylene complex, Cp2Ru2(μ-CH2)(CO)2(MeCN), with diazoalkanes (R2C=N2) leading to alkenyl complexes, Cp2Ru2(μ-CH=CR2)(μ-H)(CO)2, and alkenes, CH2=CR21", Journal of Organometallic Chemistry, 1998, pp. 71-83, vol. 569, Elsevier Science S.A.
Ammal et al., "Synergistic Dimetallic Effects in Propargylic Substitution Reaction Catalyzed by Thiolate-Bridged Diruthenium Complex", Journal of the American Chemical Society, 2005, pp. 9428-9438, vol. 127, American Chemical Society.

(Continued)

*Primary Examiner* — Yong Chu
*Assistant Examiner* — Sonya Wright

(57) ABSTRACT

An olefin metathesis process for converting a reactant olefin or a mixture of reactant olefins into one or more product olefins that are different from the reactant olefin(s). The process employs a catalyst system containing a carbene-generating agent and a bimetallic ruthenium complex comprising one or more μ-hydrido bridging ligands, and optionally containing di(t-butyl)phosphine. The catalyst system is advantageously active at process temperatures greater than 90° C. Cyclization metathesis and ring-opening polymerization metathesis are preferred olefin metathesis processes.

1 Claim, No Drawings

OTHER PUBLICATIONS

Andersen et al., "Synthesis and X-Ray Crystal Structure of Hexakis(trimethylphosphone)-tris-µ-methylene-diruthenium(III)", J. C. S. Chem. Comm., 1977, pp. 865-866.

Bennett et al., "(n6-Hexamethylbenzene)Ruthenium Complexes", Organometallic Compounds,1982, vol. 21, pp. 74-78.

Biermann et al., "New Syntheses with Oils and Fats as Renewable Raw Materials for the Chemical Industry", Angewandte Chemie International Edition, 2000, vol. 39, pp. 2206-2224, Wiley-VCH Verlag GmbH.

Braunstein et al., "2.2 Heterometallic Clusters in Catalysis", J. Metal Clusters in Chemistry, 1999, 2, pp. 616-677.

Buchowicz et al., "Catalytic Activity and Selectivity of Ru(=CHPh)C12(PCy2)2 in the Metathesis of Linear Alkenes", Journal of Molecular Catalysis A: Chemical, 1999, vol. 148, pp. 97-103, Elsevier Science B.V.

Burdett, "Renewable Monomer Feedstocks via Olefin Metathesis: Fundamental Mechanistic Studies of Methyl Oleate Ethenolysis with the First-Generation Grubbs Catalyst", Organometallics, 2004, vol. 23, pp. 2027-2047, American Chemical Society.

Cherkas et al., "A Triad of Stable, Cationic, µ-Hydrido, µ-Alkylidene Complexes, [(µ-H)M2(CO)6{µ-CHC(Ph)NEt2}(µ-PPh2)]X (M=Fe, Ru, Os; X=BF4, PF6), via the Protonation of an Alkylidene-Bridged, Electron-Rich Metal-Metal Bond", Organometallics, 1987, pp. 1466-1469, vol. 6, American Chemical Society.

Cooke et al., Synthesis, X-Ray Crystal Structure and Reactivity of the Di-µ-carbene Complex [Ru2(CO)2(µ-CHMe)(µ-CMe2)(n-C5H5)2], J. C. S. Chem. Comm., 1981, pp. 862-864.

Dias et al., "Synthesis and Investigation of Homo- and Heterobimetallic Ruthenium Olefin Metathesis Catalysts Exhibiting Increased Activities", Organometallics, 1998, pp. 2758-2767, vol. 17, American Chemical Society.

Dowden et al., "Olefin Metathesis in Non-Degassed Solvent Using a Recyclable, Polymer Supported Alkylideneruthenium", Chemical Communications, 2001, vol. 1, pp. 37-38, The Royal Society of Chemistry.

Dyke et al., "Conversion of Allene Into µ-Dimethylcarbene at a Diruthenium Centre", Journal of Organometallic Chemistry, 1980, pp. C47-C49, vol. 199, Elsevier Sequoia S.A.

Gessler et al., "Synthesis and Metathesis Reactions of a Phosphine-Free Dihydroimidazole Carbene Ruthenium Complex", Tetrahedron Letters, 2000, vol. 41, pp. 9973-9976, Elsevier Science Ltd.

Goux et al., "Ruthenium titanocene and ruthenium titanium half-sandwich bimetallic complexes in catalytic cyclopropanation", Journal of Organometallic Chemistry, 2005, pp. 301-306, vol. 690, Elsevier B.V.

Hahn, "Transition Metal Complexes Containing Bridging Alkylidene Ligands", pp. 205-264.

Herrmann, "The Methylene Bridge", Advances in Organometallic Chemistry, 1982, pp. 159-263, vol. 20, Academic Press, Inc.

Hursthouse et al., "Synthesis and X-ray Crystal Structures of Hexakis(trimethylphosphine)tris-µ-methylene-diruthenium-(III) and Its Mono- and Dicationic Derivatives, Hexakis(trimethylphosphine)-µ-methyl-bis-µ-methylene-di-ruthenium(III) Tetrafluoroborate and Hexakis(trimethylphosphine)bis-µ-methylene-diruthenium-(III) Bistetrafluroborate", Journal of the American Chemical Society, 1979, pp. 4128-4139, vol. 101 No. 15, American Chemical Society.

Jahncke et al., Dinuclear (Arene)ruthenium Hydrido Complexes: Synthesis, Structure, and Fluxionality of (C6Me6) 2Ru2H3(BH4), Organometallics, 1997, pp. 1137-1143, vol. 16, American Chemical Society.

Jones et al., "Further Chemistry of Tris(µ-methylene)-hexakis(trimethylphosphine)-diruthenium(III). Synthesis and X-Ray Crystal Structures of Bis[bis(µ-methylene)-tetrakis(trimethylphosphine)ruthenium(III)]ruthenium(IV)-(Ru-Ru-Ru) Bis (tetrafluoroborate), Tris(µ-hydroxo)-hexakis(trimethylphosphine)diruthenium(II) Tetrafluoroborate, and Tricarbonylbis (tri-methylphosphine)ruthenium(0)", J. C. S. Dalton, 1980, pp. 1771-1778.

Kingsbury et al., "A Recyclable Ru-Based Metathesis Catalyst", Journal of the American Chemical Society, 1999, vol. 121, pp. 791-799, American Chemical Society.

Le Gendre et al., "Ti-Ru bimetallic complexes: catalysts for ring-closing metathesis", Journal of Organometallic Chemistry, 2002, pp. 231-236, vol. 643-644, Elsevier Science B.V.

Mandelli et al., "Ethenolysis of Esters of Vegetable Oils: Effect of B2O3 Addition to Re2O7/SiO2.Al2O3-SnBu4 and CH3ReO3/SiO2.Al2O3 Metathesis Catalysts", Journal of the American Oil Chemical Society, 1996, vol. 73 No. 2, pp. 229-232, AOCS Press.

Maynard et al., "Purification Technique for the Removal of Ruthenium from Olefin Metathesis Reaction Products", Tetrahedron Letters, 1999, vol. 40, pp. 4137-4140, Elsevier Science Ltd.

Nubel et al., "A Convenient Catalyst System Employing RuCl3 or RuBr3 for Metathesis of Acyclic Olefins", Journal of Molecular Catalysis A: Chemical, 1999, vol. 145, pp. 323-327, Elsevier Science B.V.

Paquette et al., "A Convenient Method for Removing All Highly-Colored Byproducts Generated During Olefin Metathesis Reactions", Organic Letters, 2000, vol. 2 No. 9, pp. 1259-1261, American Chemical Society.

Refvik et al., "Ruthenium-Catalyzed Metathesis of Vegetable Oils", Journal of the American Oil Chemists' Society, 1999, vol. 76, pp. 93-98, AOCS Press.

Roscoe et al., "Functionalized Polystyrene as a Versatile Support for Olefin Polymerization Catalysts", Journal of Polymer Science: Part A: Polymer Chemistry, 2000, pp. 2979-2992, vol. 38, John Wiley & Sons, Inc.

Severin, "Asymmetric Halogeno-Bridged Complexes: New Reagents in Organometallic Synthesis and Catalysis", Chemistry: A European Journal, 2002, pp. 1514-1518, vol. 8 No. 7, Wiley-VCH Verlag GmbH.

Suss-Fink et al., "Dinuclear Ruthenium and Osmium Arene Trihydrido Complexes: Versatile Water-Soluble Synthons in Organometallic Chemistry", Organometallics, 2007, pp. 766-774, vol. 26, American Chemical Society.

Tschan et al., "Reactivity of the Unsaturated Complex [(C6Me6)2Ru2(u2-H)3]+ toward Phosphines: Synthesis and Molecular Structure of the Dinuclear Cations [C6Me6)2Ru2(u2-PR2)(u2-H)2]+ and Characterization of the P-C Bond Activation Intermediate [(C6Me6)2Ru2(u2-PPh2)(u2-H)(u2-Ph)]+", Organometallics, 2005, pp. 1974-1981, vol. 24, American Chemical Society.

Warwel et al., "Polymers and Surfactants on the Basis of Renewable Resources", Chemosphere, 2001, vol. 43, pp. 39-48, Elsevier Science Ltd.

Weck et al., "Synthesis of ABA Triblock Copolymers of Norbornenes and 7-Oxanorbornenes via Living Ring-Opening Metathesis Polymerization Using Well-Defined, Bimetallic Ruthenium Catalysts", Macromolecules, 1996, pp. 1789-1793, vol. 29, American Chemical Society.

Weiss et al., "Untersuchungen von Polymerisations- und Metathese-Reaktionen: XIV Darstellung heterogener, bimetallischer Metathese-Katalysatoren durch Reaktionen von Carbin-Wolfram-Komplexen des Fischer-Typs mit reduziertem Phillips-Katalysator", Journal of Organometallic Chemistry, 1988, pp. 273-280, vol. 355, Elsevier Sequoia S.A.

Weskamp et al., "Highly Active Ruthenium Catalysts for Olefin Metathesis: The Synergy of N-Heterocyclic Carbenes and Coordinatively Labile Ligands", Angewandte Chemie Int. Ed., 1999, pp. 2416-2419, vol. 38 No. 16, Wiley-VCH Verlag GmbH.

Yao, "A Soluble Polymer-Bound Ruthenium Carbene Complex: A Robust and Reusable Catalyst for Ring-Closing Olefin Metathesis", Angewandte Chemie International Edition, 2000, vol. 39, pp. 3896-3898, Wiley-VCH Verlag GmbH.

* cited by examiner

OLEFIN METATHESIS PROCESS EMPLOYING BIMETALLIC RUTHENIUM COMPLEX WITH BRIDGING HYDRIDO LIGANDS

CROSS-REFERENCE TO RELATED APPLICATION(S)

This application claims benefit of priority from U.S. Provisional Patent Application No. 61/110,158, filed Oct. 31, 2008, which application is incorporated by reference herein in its entirety.

FIELD OF THE INVENTION

This invention pertains to an olefin metathesis process employing a catalyst system comprising a bimetallic ruthenium-ligand complex.

BACKGROUND OF THE INVENTION

Olefin metathesis is a well-known process wherein one or more olefinically-unsaturated reactants are contacted with a metathesis catalyst under reaction conditions sufficient to cleave one or more of the carbon-carbon double bond(s) in the olefinically-unsaturated reactant(s), after which the resulting molecular fragments are reformed into one or more olefinically-unsaturated products that are different from the olefinically-unsaturated reactant(s). The prior art teaches various classes of olefin metathesis processes including self-metathesis (SM), cross-metathesis (CM), acyclic ring-closing or cyclization metathesis (RCM), ring-opening polymerization metathesis (ROMP), and polymer segment interchange metathesis (PSIM).

Recent interest in olefin metathesis chemistry has led to a number of published patent applications. For example, WO 2008/027267 A2 relates to production of metathesis products by high melting polymer segment interchange. WO 2008/027268 A2 relates to production of metathesis products by amorphous polymer segment interchange. WO 2008/027269 A2 relates to production of telechelic compounds by metathesis depolymerization. WO 2008/027283 A2 relates to production of meta-block copolymers by polymer segment interchange. WO 2009/0091588 A2 relates to metathetic production of functionalized polymers.

Many prior art catalysts are single component catalysts consisting of a single site ruthenium-ligand complex comprising one ruthenium atom, a plurality of anionic and/or neutral ligands, for example, halide(s) and phosphine(s) ligands, and one carbene (alkylidene) group of formula: $CR^aR^b$ bonded to the ruthenium atom, wherein $R^a$ and $R^b$ are independently selected from hydrogen and C1-C20 hydrocarbyl groups. Single site ruthenium complex-catalyzed metathesis processes are illustrated in the following prior art references: WO 96/04289, U.S. Pat. No. 7,102,047, and Thomas Weskamp, et al., *Angewandte Chemie Int. Ed.,* 1999, 38, pp. 2416-2419. Single site ruthenium complex catalysts tend to exhibit decreased activity at elevated temperatures, for example, at temperatures greater than 90° C.

Other prior art references disclose the use of bimetallic catalysts or bimetallic catalyst precursors in metathesis processes. These catalysts or catalyst precursors include homo-bimetallic ruthenium complexes containing two ruthenium atoms and hetero-bimetallic complexes containing one ruthenium atom and a different metallic atom, such as Ti or W. Terminal ligands on each of the metal atoms include one or more anionic and/or neutral ligands, such as halide(s) and/or phosphine(s); whereas ligands bridging the two metal atoms embrace many diverse species including halides, dithiolates, phosphine-substituted cyclopentadienyl, or bisalkylidene-substituted phenyl groups. These bimetallic metal complexes generally do not contain a metal-metal bond, but contain instead two discrete metal centers within a single complex. Where the bimetallic complex comprises one or more alkylidene ligands bonded to one of the ruthenium atoms, no other catalytic component is required. Where the bimetallic complex comprises no alkylidene ligand bonded to a ruthenium atom, then the complex may be considered to be a catalyst precursor, and a co-catalyst is usually required. The co-catalyst is advantageously a carbene or alkylidene-generating agent, such as a propargyl compound.

The following prior art references illustrate a variety of homo and hetero bimetallic metathesis catalysts and catalyst precursors: Eric L. Dias, et al., *Organometallics,* 1998, 17, pp. 2758-2767; Kay Severin, Chem. Euro. J., 2002, 8, pp. 1515-1518; Salai Cheettu Ammal, et al, *Journal of the American Chemical Society,* 2005, 127, pp. 9428-9438; Pierre Le Gendre, et al., *Journal of Organometallic Chemistry,* 2002, 643-644, pp. 231-236; and Jérôme Goux, et al., *Journal of Organometallic Chemistry,* 2005, 690, pp. 301-306; Marcus Weck, et al., *Macromolecules,* 1996, 29, pp. 1789-1793, as well as previously cited WO-A1-96/04289.

Other prior art references, such as Munetaka Akita, et al., *Journal of Organometallic Chemistry,* 1998, 569, pp. 71-78, teach carbon-carbon coupling from labile diruthenium bridging μ-methylene complexes. Other references teach crystallographic structures or various reactivities of diruthenium bridging μ-alkylidene or μ-hydrido complexes. See, for example, Andrew A. Cherkas, Organometallics, 1987, 6, pp. 1466-1469; Manfred Jahncke, et al., *Organometallics,* 1997, 16, pp. 1137-1143; and Mathieu J.-L. Tschan, et al., *Organometallics,* 2005, 24, pp. 1974-1981.

Despite various disclosures to date, the art would benefit from the discovery of new ruthenium metathesis catalysts, particularly, those having an improved reactivity at higher operating temperatures, preferably, greater than about 90° C. Operation at higher temperatures affords faster reaction rates and easier removal of solvent(s) employed in the process, by reducing temperature cycling between the metathesis operating temperature and the temperature needed for solvent separation.

SUMMARY OF THE INVENTION

In a more specific aspect, this invention pertains to a process of ring-opening metathesis polymerization (ROMP) in the presence of the catalyst system comprising a bimetallic ruthenium-ligand complex. In another specific aspect, this invention pertains to a process of ring-closing metathesis (RCM or cyclization metathesis) in the presence of the catalyst system comprising a bimetallic ruthenium-ligand complex.

In one aspect, this invention provides for an olefin metathesis process comprising contacting one or more olefinically-unsaturated reactants with a metathesis catalyst system under reaction conditions sufficient to prepare one or more olefinically-unsaturated products that are different from the olefinically-unsaturated reactant(s). The catalyst system useful in the process of this invention comprises a carbene-generating agent, a bimetallic ruthenium-ligand complex represented by Formula I hereinafter:

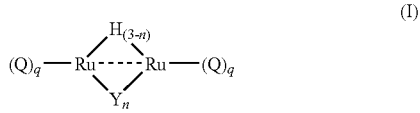

(I)

wherein each q is 1; each Q is independently selected from 6-electron donor arene ligands; wherein each n is the same and is 0, 1, or 2; wherein each Y is an anionic di(t-butyl) phosphido ligand, with the proviso that when n=0, then the catalyst system further comprises di(tertiary-butyl)phosphine.

In a related aspect, this invention provides for a process of ring-opening metathesis polymerization comprising contacting an olefinically-unsaturated cyclic compound having at least one internal carbon-carbon double bond with the aforementioned catalyst system, the contacting being conducted under reaction conditions sufficient to prepare an olefinically-unsaturated polymer.

In another related aspect, this invention provides for a process of ring-closing metathesis comprising contacting an olefinically-unsaturated acyclic diene with the aforementioned catalyst system, the contacting being conducted under reaction conditions sufficient to prepare an olefinically-unsaturated cyclic compound.

In yet another related aspect, this invention provides for ethenolysis of an olefinically-unsaturated fatty acid or olefinically-unsaturated fatty acid ester, the process comprising contacting said olefinically-unsaturated fatty acid or ester with ethylene in the presence of the aforementioned catalyst system, the contacting occurring under process conditions sufficient to prepare a reduced-chain unsaturated acid or ester.

In yet another related aspect, this invention pertains to a polymer interchange olefin metathesis process comprising contacting an olefinically-unsaturated polymer or a mixture of olefinically-unsaturated polymers, optionally in the presence of ethylene, in the presence of the aforementioned catalyst system, the contacting being conducted under reaction conditions sufficient to prepare an olefinically-unsaturated polymer product composition different from the olefinically-unsaturated reactant polymer(s).

The processes of this invention advantageously provide for industrially-useful olefins by reforming one or a mixture of olefinic feedstocks. The processes can be advantageously conducted at elevated operating temperatures greater than 90° C., preferably, greater than 100° C., and more preferably, greater than 110° C., which allows for ready removal of any solvent(s) employed in the process.

DETAILED DESCRIPTION OF THE INVENTION

Certain phrases, terms, and words used in this application are defined hereinafter. When interpreting a meaning of a phrase, term, or word, its definition here governs unless, for a particular use, a different meaning is stated elsewhere in this specification or unless a context of the use of the phrase, term, or word clearly indicates a different meaning is intended from the definitions provided herein.

The articles "a" and "the" refer to singular and plural forms of what is being modified by the articles. When used in front of a first member of a list of two or more members, the words "a" and "the" independently refer to each member in the list. As used herein, "a," "an," "the," "at least one," and "one or more" are used interchangeably. The term "comprises" and variations thereof do not have a limiting meaning where these terms appear in the description and claims. Thus, for example, a reactant mixture that comprises an olefin can be interpreted to mean that the olefin includes "one or more" olefins.

All percentages, preferred amounts or measurements, ranges and endpoints thereof are inclusive, that is, "a range from 5 to 10" includes 5 and 10. "At least" is equivalent to "greater than or equal to," and "at most" is, thus, equivalent to "less than or equal to." Numbers herein have no more precision than stated. Thus, "115" includes at least from 114.6 to 115.4. All ranges from a parameter described as "at least," "greater than," "greater than or equal to" or similarly, to a parameter described as "at most," "up to," "less than," "less than or equal to" or similarly are preferred ranges regardless of the relative degree of preference indicated for each parameter. Thus a range that has an advantageous lower limit combined with a most preferred upper limit is preferred for the practice of this invention. The term "advantageously" is used to denote a degree of preference more than required, but less than is denoted by the term "preferably."

Except in the examples, or where otherwise indicated, all numbers expressing quantities, percentages, properties, functionalities and so forth in the specification are to be understood as being modified in all instances by the term "about." Unless stated otherwise, when an element, material, or step capable of causing undesirable effects is present in amounts or in a form such that it does not cause the effect to an unacceptable degree, that element, material, or step is considered substantially absent for the practice of this invention. Those skilled in the art recognize that acceptable limits vary with equipment, conditions, applications, and other variables, but are determinable without undue experimentation in each situation where they are applicable. In some instances, variation or deviation in one parameter is acceptable to achieve another desirable end.

As used herein, the phrase "having the formula" or "represented by the formula" is not intended to be limiting and is used in the same manner as the term "comprising" is commonly used.

The term "comprising," is synonymous with "including," "containing," or "characterized by," is inclusive or open-ended and does not exclude additional, unrecited elements, material, or steps. The term "consisting essentially of" indicates that in addition to specified elements, materials, or steps, unrecited elements, materials or steps are optionally present in amounts that do not unacceptably materially affect at least one basic and novel characteristic of the subject matter. The term "consisting of" indicates that only stated elements, materials or steps are present except that unrecited elements, materials or steps are optionally present to an extent that has no appreciable effect, or are substantially absent.

The word "optionally" means "with or without," as in not obligatory and left to one's choice. As an example, to say "optionally, a diluent" means with or without a diluent.

The words "the process" or the words "the metathesis process" as used hereinafter refer to the olefin metathesis process of this invention as described herein.

The number of carbon atoms or a range thereof forming a moiety or compound is defined by prefixing the moiety or compound with a formula "$C_m$" or "$C_m$-$C_n$," respectively, wherein m and n are integers. For example, a $C_1$-$C_{10}$ hydrocarbyl means the hydrocarbyl has a number of carbon atoms in a range from one (1) to ten (10) carbon atoms.

Abbreviations and symbols "g," "hr," "L," "ml," "mol," "mmol," "NMR," "° C.," psig (kPa), and "%" are used, respectively, for "gram," "hour," "liter," "milliliter," "mole," "millimole," "nuclear magnetic resonance," "degree Celsius," pounds per square inch gauge (kilo Pascals), and "percent," respectively, and plural forms thereof.

Any reference to the Periodic Table of the Elements herein shall refer to the Periodic Table of the Elements published in *Nomenclature of Inorganic Chemistry: IUPAC Recommendations* 2005, Royal Society of Chemistry, 2005, ed. N. G. Connelly and T. Damhus. Also, any reference to a Group or Groups shall be to the Group or Groups reflected in this Periodic Table of the Elements using the IUPAC system for numbering groups.

The relevant teachings of each reference cited herein are incorporated to the maximum extent allowed by United States law. In the event of a conflict between a portion of an incorporated reference and this Application, this Application takes precedence.

In the detailed description that follows, several chemical terms may be used that for clarity are defined herein.

"Olefin metathesis" refers to a process wherein one or more olefinically-unsaturated reactants are contacted with a metathesis catalyst under reaction conditions sufficient to cleave one or more of the carbon-carbon double bond(s) in the olefinically-unsaturated reactant(s), after which the resulting molecular fragments are reformed into one or more olefinically-unsaturated products that are different from the olefinically-unsaturated reactant(s). The phrase "different from the olefinically-unsaturated reactant" refers to the interchange of the molecular fragments such that the structure of the olefinically-unsaturated reactant—i.e., the substance or composition from which the molecular fragments are cleaved—is not the same as the structure of the olefinically-unsaturated product—i.e., the substance or composition that is formed from the molecular fragments. Such structural difference(s) can be detected and characterized by employing one or more conventional analytical techniques that are suitable for indirectly or, preferably, directly characterizing structures of olefins or polyolefins. Such analytical techniques are, for example, iodine monochloride titration; nuclear magnetic resonance (NMR) spectroscopy (preferably proton- or carbon-13 NMR, more preferably carbon-13 NMR); infrared spectroscopy; and techniques suitable for determining number average molecular weight.

"Self-metathesis" refers to reaction between two identical molecules of olefinically-unsaturated reactant to obtain one or more olefinic products different from the reactant. "Cross-metathesis" refers to the reaction of one olefinically-unsaturated reactant with a second chemically-distinct olefinically-unsaturated reactant to prepare one or more olefinically-unsaturated products different from the reactants. "Acyclic ring-closing metathesis" or "cyclization metathesis" refers to reforming an acyclic olefinically-unsaturated diene to form a ring compound containing an internal unsaturated carbon-carbon double bond. "Ring-opening metathesis polymerization" refers to reforming an olefinically-unsaturated ring compound containing one or more internal carbon-carbon double bonds to produce an acyclic unsaturated polymer. "Polymer segment interchange metathesis" refers to reforming one or more olefinically-unsaturated reactant polymers via cleavage at the carbon-carbon double bonds and recombination of the resulting polymeric segments to form new olefinically-unsaturated polymer product composition(s).

A "hydrocarbyl" moiety is defined as a monovalent moiety derived from a hydrocarbon by removal of one hydrogen atom from one carbon atom. A "hydrocarbon" shall have its ordinary meaning referring to a compound composed of carbon and hydrogen atoms. A hydrocarbyl can be an alkyl, alkenyl, alkynyl, or aryl, which is defined as a monovalent moiety derived from an alkane, alkene, alkyne, or arene, respectively, by removal of one hydrogen atom from one carbon atom. An alkyl can be a primary alkyl, secondary alkyl, or tertiary alkyl, which has two or three hydrogen atoms, one hydrogen atom, or no hydrogen atom, respectively, on the carbon atom that forms the alkyl.

A "hydrocarbylene" moiety is defined as a divalent moiety derived from a hydrocarbon by removal of two hydrogen atoms from two carbon atoms.

The term "alkyl" refers to a saturated monovalent hydrocarbyl radical, which may be linear, branched, or cyclic (alicyclic). If linear or branched, the radical typically contains from 1 to about 30 carbon atoms, for example, methyl, ethyl, propyl, isopropyl, butyl, iso-butyl, tert-butyl, and the like. If cyclic (alicyclic), the radical typically contains from 4 to about 8 carbon atoms, such as cyclobutyl, cyclopentyl, cyclohexyl, cycloheptyl, and cyclooctyl. Preferably, the linear or branched alkyl radical contains from about 1 to about 12 carbon atoms; and the alicyclic radical contains from about 5 to about 7 carbon atoms, exclusive of carbon-containing substituents.

The term "alkylene" as used herein refers to a linear, branched, or cyclic divalent alkyl radical.

The term "aromatic" or "arene" refers to a polyatomic, cyclic, conjugated ring compound containing $(4\delta+2)$ $\pi$-electrons, wherein $\delta$ is an integer greater than or equal to 1. The arene can contain a single aromatic ring or multiple aromatic rings that are fused together or directly linked, or indirectly linked (such that different aromatic groups are bound through a common group, such as methylene or ethylene). Preferred arenes or aromatic compounds contain from 6 to about 25 carbon atoms (C6-C25), including alkyl substituents. Preferably, for the bimetallic ruthenium complexes of this invention, $\delta=1$, and the arene is a 6 $\pi$-electron donor ligand. Examples of arenes include benzene, toluene, xylenes, ethylbenzene, isopropylbenzene, and trimethylbenzenes, among others.

The term "aryl" refers to a monovalent aromatic radical containing a single aromatic ring or containing multiple aromatic rings that are fused together or directly linked, or indirectly linked (such that different aromatic groups are bound through a common group, such as methylene or ethylene), which is formed by removing one hydrogen atom from a ring carbon of an aromatic compound or arene. Preferred aryl radicals contain one aromatic ring, or 2 to 4 fused or linked aromatic rings, for example, phenyl, naphthyl, biphenyl, and the like.

The term "arylene" refers to a divalent aryl radical.

The term "aralkyl" or "arylalkyl" refers to a monovalent alkyl radical substituted with at least one aryl radical. The term "aralkylene" refers to a divalent alkylene radical substituted with at least one aryl radical.

The term "arylalicyclic" refers to an alicyclic radical substituted with at least one aryl group. An example of an arylalicyclic radical is "phenylcyclohexyl" or "phenylcyclopentyl." Typically, the arylalicyclic radical contains greater than about 10 carbon atoms and less than about 20 carbon atoms.

The term "alkaryl" refers to a monovalent aryl radical with one or more alkyl substituents. The term "alkarylene" refers to a divalent aryl radical with one or more alkyl substituents.

As used herein, any and all of the terms "hydrocarbyl," "hydrocarbylene," "alkyl," "alkylene," "aryl," "arylene," "alkaryl," "alkarylene," "aralkyl," "aralkylene," "alicyclic," and "arylalicyclic" are intended to include substituted variants thereof. The term "substituted" or the words "substituted variants thereof" refer to replacement of one or more H or C atoms in the hydrocarbyl or any other aforementioned radical by one or more heteroatoms or one or more functional groups that contain one or more heteroatoms, including but are not limited to nitrogen, oxygen, sulfur, phosphorus, boron, chlorine, bromine, and iodine. For example, "alkoxy" substitution refers to an alkyl radical bonded at one end to an oxygen atom; and "halo" substitution refers to replacement of a hydrogen atom by a chloro, bromo, or iodo atom.

In one aspect, this invention provides for an olefin metathesis process comprising contacting one or more olefinically-unsaturated reactants with a metathesis catalyst system under reaction conditions sufficient to prepare one or more olefinically-unsaturated products that are different from the olefinically-unsaturated reactant(s). The catalyst system for this invention comprises a carbene-generating agent, a bimetallic ruthenium-ligand complex represented by Formula I hereinafter:

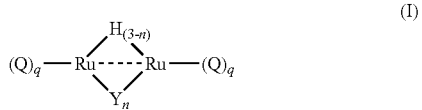

(I)

wherein each q is 1; each Q is independently selected from 6-electron donor arene ligands; wherein each n is the same and is 0, 1, or 2; wherein each Y is an anionic di(t-butyl) phosphido ligand, with the proviso that when n=0, then the catalyst system further comprises di(tertiary-butyl)phosphine. The bimetallic Ru complex of Formula I generally has a positive charge characteristic of a cation, preferably +1, and therefore, further comprises one or more charge-balancing anions, preferably, a monovalent anion of −1 charge.

In a related aspect, this invention provides for a process of ring-opening metathesis polymerization comprising contacting an olefinically-unsaturated cyclic compound having at least one internal carbon-carbon double bond with the aforementioned catalyst system, the contacting being conducted under reaction conditions sufficient to prepare an olefinically-unsaturated polymer.

In another related aspect, this invention provides for a process of ring-closing metathesis comprising contacting an olefinically-unsaturated acyclic diene with the aforementioned catalyst system, the contacting being conducted under reaction conditions sufficient to prepare an olefinically-unsaturated cyclic compound.

In yet another related aspect, this invention provides for ethenolysis of an olefinically-unsaturated fatty acid or olefinically-unsaturated fatty acid ester, the process comprising contacting said olefinically-unsaturated fatty acid or ester with ethylene in the presence of the aforementioned catalyst system, the contacting occurring under process conditions sufficient to prepare a reduced-chain unsaturated acid or ester.

In yet another related aspect, this invention pertains to a polymer interchange olefin metathesis process comprising contacting an olefinically-unsaturated polymer or a mixture of olefinically-unsaturated polymers, optionally in the presence of ethylene, in the presence of the aforementioned catalyst system, the contacting being conducted under reaction conditions sufficient to prepare an olefinically-unsaturated polymer product composition different from the olefinically-unsaturated reactant polymer(s).

Any organic compound containing one or more unsaturated carbon-carbon double bonds (>C=C<), that is, any olefinically-unsaturated compound, may be suitably employed in the olefin metathesis process of this invention. Monoolefins and diolefins (dienes) are preferably employed. Depending upon the olefin metathesis process selected, one olefinic reactant may be employed for self-metathesis, ring-closing, and ring-opening olefin metathesis processes defined hereinabove; or alternatively, a mixture of olefinic reactants may be employed for cross-metathesis and polymer interchange olefin metathesis processes defined hereinabove. The reactant olefin may comprise an acyclic (straight or branched) carbon skeleton containing a terminal or an internal carbon-carbon double bond. Terminal double bonds involve a carbon-carbon double bond between the α and β carbon atoms of the olefin; whereas internal double bonds involve a carbon-carbon double bond at β,γ-carbon atoms or two other adjacent internal carbon atoms of the chain. Alternatively, a cyclic olefin may be employed comprising an olefinically-unsaturated cyclic hydrocarbon or an olefinically-unsaturated heterocyclic compound, wherein at least one carbon-carbon double bond is present involving two adjacent carbon atoms in the ring cycle.

Acyclic olefinically-unsaturated reactants advantageously employed in this process comprise C2-C30 olefinic hydrocarbons, preferably, C2-C-20 olefinic hydrocarbons, more preferably, C2-C10 olefinic hydrocarbons, including terminal and internal isomers thereof and substituted variants thereof. Non-limiting examples of such acyclic mono-olefinic reactants include propylene, butene, pentene, hexene, heptene, octene, nonene, decene, dodecene, and higher homologues thereof, including both terminal and internal unsaturated isomers thereof. Non-limiting examples of acyclic diene reactants include butadiene, hexadiene, octadiene, diethyl diallyl malonate, and higher homologues thereof. In some embodiments, the acyclic olefinically-unsaturated reactant is the acyclic diene reactant that is diethyl diallyl malonate. Acid, ester, aldehyde, and hydroxy substituted variants of all of the aforementioned species comprise another preferred class of reactant olefins. Mono-, di-, and tri-unsaturated fatty acids and fatty acid esters having from about 6 to about 30 carbon atoms per fatty acid chain are also preferred reactant olefins for self-metathesis and cross-metathesis processes, preferably, ethenolysis. Of the fatty acid esters, the glyceride esters, the esters of pentaerythritol, and the esters of C1-C10 mono-alkanols are particularly preferred. Oleic acid and C1-C5 alkyl oleate are more preferred fatty acid and fatty acid ester, respectively, with methyl oleate being most preferred.

Cyclic olefins that are advantageously employed in the process of this invention include monocyclic and polycyclic olefins advantageously comprising about C4-C25 carbon atoms, preferably, C4-C12 carbon atoms, and more preferably, C4-C10 carbon atoms. The cyclic olefin is characterized as having at least one internal olefinically-unsaturated C=C bond. Cyclic mono-olefins and cyclic-dienes are more preferred. Non-limiting examples of cyclic olefins include cyclopentene, cyclopentadiene, cyclohexene, cyclohexadiene, cycloheptene, cyclooctene, cyclooctadiene, 2-ethylcyclohexene, and 2-ethylcyclohexadiene.

Olefinically-unsaturated polymers that may be suitably employed in the olefin metathesis process of this invention comprise any polymer containing a carbon-carbon double bond. The term "polymer" as used herein refers to a macromolecular compound comprising multiple repeating units and a molecular weight of at least 500 grams per mole (g/mol), preferably at least 1000 g/mol. The upper limit on molecular weight is not particularly critical. Advantageously, the polymer has a molecular weight less than 1,000,000 g/mol. In some embodiments, the polymer has a molecular weight of at least 500 g/mol and less than 1,000,000 g/mol. As used herein, the term "molecular weight" when referring to the polymer means number average molecular weight and is determined by the method described later. Preferably, at least one repeating unit occurs, consecutively or non-consecutively, 6 or more times, more preferably 10 or more times, and most preferably 20 or more times on average. Molecules containing less than 6 such repeating units on average are referred to herein as oligomers. The term "polymers" includes homopolymers, copolymers, terpolymers, interpolymers, and so on. The term "interpolymer" may be used interchangeably with the term "copolymer" to refer to polymers incorporating in polymerized form at least two differentiated repeating units, usually obtained from separate copolymerizable monomers. The least prevalent monomer, on a mole percent basis, in the resulting copolymer or interpolymer is generally referred to by the term "comonomer." It is noted that where two or more unsaturated polymers are employed in polymer segment interchange metathesis, the resulting polymeric product may exhibit an average molecular weight not much changed from the reactant mixture of polymers. In contrast, if a polymer is employed in an olefin metathesis process with a lower olefinic reactant, such as ethylene, the resulting polymeric product exhibits a reduced average molecular weight as compared with the reactant polymer.

If two olefinically-unsaturated compounds are employed in the process, then the relative mole quantities of either one to the other advantageously range from about 0.5/1 to about 2/1 on a molar basis, and preferably, from about 0.8/1 to about 1.3/1, and more preferably, from about 0.90/1 to about 1.1/1.

Advantageously, a solvent is employed in the olefin metathesis process, although a solvent is not required. A solvent may be desirable, for instance, to solubilize solid olefinically-unsaturated reactants, or to solubilize reactants when one is not entirely miscible with the other, or to solubilize reactants in different phases (e.g., ethylene and unsaturated polymer). The solvent is also employed to solubilize the components of the catalyst system, namely, the carbene-generating agent, the bimetallic ruthenium-ligand complex, and the di(t-butyl) phosphine, if present, and to facilitate formation of the catalytically active species and its contact with the olefinically-unsaturated reactants. The solvent can be any thermally stable and chemically stable liquid that also solubilizes at least one of the olefinically-unsaturated reactants. The term "thermally stable" means that the solvent does not substantially decompose at operating process temperature. The term "chemically stable" means that the solvent is substantially non-reactive with the olefinically-unsaturated reactants and the products of the process; and the term also implies that the solvent does not substantially coordinate with or bond to the metathesis catalyst or catalyst precursor components in a way that inhibits or impedes catalyst performance. Non-limiting examples of suitable solvents include aromatic hydrocarbons, such as benzene, toluene, and xylenes; chlorinated aromatic hydrocarbons, preferably chlorinated benzenes, such as chlorobenzene and dichlorobenzene; alkanes, such as pentane, hexane, heptane, cyclopentane, and methylcyclohexane; and chlorinated alkanes, such as methylene dichloride, chloroform, and carbon tetrachloride. If a solvent is used, then any amount can be employed, provided that the olefin metathesis process proceeds as desired. The concentration of at least one olefinically-unsaturated reactant in the solvent is advantageously greater than about 0.05 molar (M; also called molarity), preferably, greater than about 0.5 M, and advantageously less than about the saturation concentration, preferably, less than about 5.0 M.

Advantageously, the process of this invention is conducted under an inert atmosphere so as to minimize interference or poisoning of the catalyst system by oxygen. The inert atmosphere comprises any gas or gaseous mixture that is inert with respect to the olefin metathesis process. Suitable inert atmospheres include, without limitation, helium, neon, argon, nitrogen, and mixtures thereof.

If any olefinically-unsaturated reactant is provided to the olefin metathesis process as a gas, as will be the case when ethylene is employed in an ethenolysis metathesis, then that gaseous reactant may be fed to the reactor as an essentially pure gaseous stream or in a stream diluted with a gaseous diluent. As the gaseous diluent, any gas that is inert towards the olefin metathesis process and catalyst system may be used, suitable examples of which include, without limitation, helium, neon, argon, nitrogen, and mixtures thereof. The concentration of gaseous olefinically-unsaturated reactant in the gaseous diluent may be any that provides for an operable olefin metathesis process. Suitable concentrations are advantageously greater than about 5 mole percent, and preferably, greater than about 10 mole percent olefinic reactant, and advantageously less than 90 mole percent, based on total moles olefinic reactant and gaseous diluent.

The catalyst system of this invention requires two components, namely, a carbene-generating agent and a bimetallic ruthenium-ligand complex of Formula I, and may further comprise a third component in the form of di(tertiary-butyl) phosphine, (t-Bu)$_2$PH. At the present time each catalyst component is considered to be a catalyst precursor, which taken altogether under process conditions generates a catalytically-active species, most likely but not definitely, a ruthenium-alkylidene complex. Whether the catalytically-active species is a single site ruthenium complex or a bimetallic ruthenium complex is not known at this time; although based on the performance of the catalyst at elevated temperatures, it is believed that the active catalytic species retains at least some bimetallic character and may further contain a metal-metal (i.e., Ru—Ru) bond. Whether a metal-metal bond is present and is formally a single, double, or triple bond is presently not known. The aforementioned discussion is not meant to limit the catalyst system or catalytically-active species in any manner; but rather to inform the skilled person of the various possible forms of the active catalyst.

The carbene-generating agent comprises an organic compound capable of producing a carbene moiety, advantageously, a carbene moiety represented by the following formula (:C=CR$_2$X), wherein R and X are defined hereinafter. Preferably, the carbene-generating agent is represented by the following Formula II:

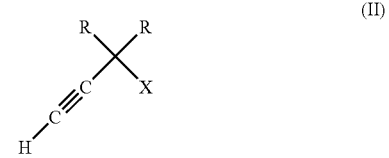

wherein each R is independently selected from hydrogen and monovalent C1-C20 hydrocarbyl groups and substituted variants thereof, preferably, hydrogen, C1-C5 alkyl, and C6-C10 aryl groups; or alternatively, wherein both R groups are bonded together to form a divalent C3-C8 alkylene or divalent C4-C7 arylene group, or substituted variant thereof; and wherein X is either hydroxyl (OH) or halogen, preferably, chlorine. Non-limiting examples of suitable and preferred carbene-generating agents include 3-chloro-3-methyl-1-butyne, 2-methyl-3-butyn-2-ol, and 1-ethynyl-1-cyclohexanol.

The carbene-generating agent is advantageously added to the catalyst system in a molar ratio greater than about 0.8/1, and preferably greater than about 0.9/1, relative to the bimetallic ruthenium-ligand complex. The carbene-generating agent is advantageously added to the catalyst system in a molar ratio less than about 2.0/1, more preferably, less than about 1.5/1, relative to the bimetallic ruthenium-ligand complex. Most preferably, the molar ratio of carbene-generating agent to bimetallic ruthenium complex is about 1.0/1.0.

The bimetallic Ru-ligand complex has been illustrated generically hereinabove in Formula I. The complex preferably comprises or can be derived from [η$^6$-arene)$_2$Ru$_2$(μ$_2$-H)$_3$]+ cationic species, the charge balance being provided by any suitable anion, such as hexafluorophosphate (PF$_6$)$^-$, tetraphenylborate (BΦ$_4$)$^-$, tetrafluoroborate (BF$_4$)$^-$, and sulfate (SO$_4$)$^{2-}$, preferably, a monovalent anion of −1 charge. Notably, the complex comprises from 1 to 3 hydrido ligands bridging the two ruthenium atoms (i.e., μ$_2$-hydrido) and from 0 to 2 anionic phosphido ligands bridging the two ruthenium atoms (i.e., μ$_2$-phosphido), the phosphido ligand being specifically di(t-butyl)phosphido, (>P(t-butyl)$_2$)$^-$.

The bimetallic ruthenium-ligand complexes with bridging hydrido ligands, and no bridging phosphido ligands, are known in the art, as are methods of preparing such complexes. See, for example, M. Jahncke, et al., *Organometallics*, 1997, 16, 1137-1143, and Mathieu J.-L. Tschan, et al., *Organometallics*, 2005, 24, 1974-1981, the aforementioned citations being incorporated herein by reference. Bimetallic ruthenium-ligand complexes containing bridging anionic (t-butyl) phosphido ligands can be synthesized from corresponding tri-μ-hydrido bimetallic ruthenium-ligand complexes by contacting the tri-hydrido bimetallic species with di(t-butyl) phosphine, (t-Bu)PH. Notably, di(t-butyl)phosphine contains one labile P—H bond which is capable of reacting with the tri-hydrido ruthenium-ligand complex to yield a μ-hydrido, μ-phosphido bimetallic ruthenium-ligand complex. The synthesis can be made in situ by simply adding di(t-butyl)phosphine to the metathesis reaction mixture containing the reactant olefin(s), the carbene-generating agent, and the tris-μ-hydrido bimetallic ruthenium-ligand complex. If di(t-butyl) phosphine is added in situ, then the molar ratio of di(t-butyl) phosphine to bimetallic ruthenium-ligand complex is advantageously greater than about 0.7/1, preferably, greater than about 0.9/1, and advantageously, less than about 3.0/1, and preferably, less than about 2.0/1. Alternatively, the bridging phosphido complex can be prepared in a separate step and then isolated; and thereafter added to the olefin metathesis process solely with the carbene-generating agent.

In addition to the bridging hydrido and phosphido ligands, each ruthenium center in the bimetallic ruthenium-ligand complex comprises an additional neutral 6-electron donor ligand to satisfy the coordination number of each ruthenium atom. The additional ligand, labeled "Q" in Formula I, comprises an arene ligand, preferably, a benzene ligand or substituted variant thereof. Preferred ligands include benzene and C1-C20-substituted benzenes, such as 1,3,5-trimethylbenzene, 1,3,5-diethylbenzene, 1,3,5-tri-isopropylbenzene, 1,3, 5-propylbenzene, 1-methyl-4-isopropylbenzene, 1-ethyl-4-isopropylbenzene, 1,2,3,4,5,6-hexamethylbenzene, 1,2,3,4, 5,6-hexaethylbenzene, and 1,2,3,4,5,6-hexapropylbenzene, and 1,2,3,4,5,6-hexa-isopropylbenzene, as well as fused ring systems, such as indane.

Preferred species of bimetallic ruthenium complexes include the following, noting that the hexafluorophosphate anion can be replaced with any equivalent monovalent anion of −1 charge:

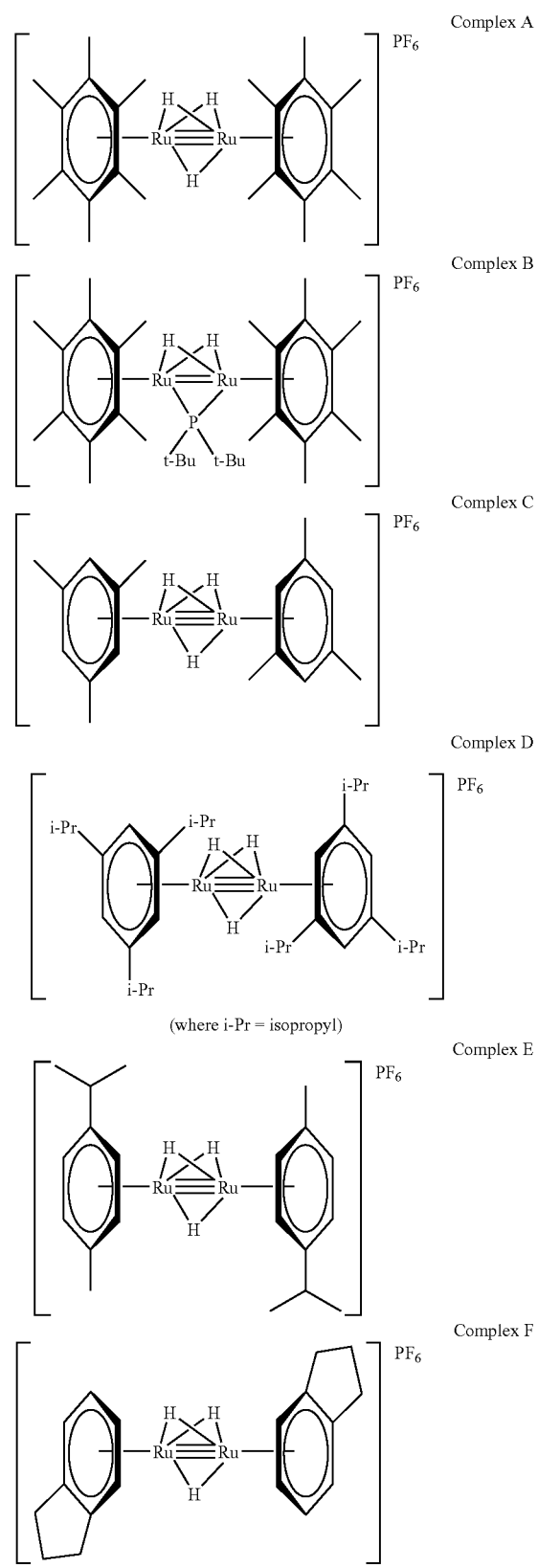

In another embodiment, the bimetallic ruthenium-ligand complex may be bound to or deposited on a solid support. The solid support advantageously simplifies recovery of the ruthenium component. In addition, the solid support can increase strength and attrition resistance of particles of the bimetallic ruthenium-ligand complex. Suitable supports include, without limitation, silicas, aluminas, silica-aluminas, aluminosilicates, including zeolites and other crystalline porous aluminosilicates; as well as titanias, zirconia, magnesium oxide, carbon, and cross-linked, reticular polymeric resins, such as functionalized cross-linked polystyrenes, e.g., chloromethyl-functionalized cross-linked polystyrenes. The bimetallic ruthenium-ligand complex can be deposited onto the support by any method known to those skilled in the art including, for example, impregnation, ion-exchange, deposition-precipitation, and vapor deposition; or can be chemically bound to the support via one or more covalent chemical bonds. Methods for chemically binding organometallic complexes to polymeric supports are well known in the art, as disclosed, for example, by Stephen B. Roscoe, et al., *Journal of Polymer Science: Part A: Polym. Chem.*, 2000, 38, 2979-2992, and by Mahmood Ahmed, et al., *Tetrahedron Letters*, 1999, 40, 8657-8662, incorporated herein by reference.

If a support is used, the bimetallic ruthenium-ligand complex can be loaded onto the catalyst support in any amount suitable for preparing the active catalyst for the olefin metathesis process. The complex is advantageously loaded onto the support in an amount greater than about 0.01, and preferably, greater than about 0.05 weight percent ruthenium, based on the total weight of the complex plus support. The catalyst is advantageously loaded onto the support in an amount less than about 20, and preferably, less than about 10 weight percent ruthenium, based on the total weight of the complex and support.

The olefin metathesis process can be conducted in any conventional reactor suitably designed for an olefin metathesis process including, for example, batch reactors, continuous stirred tank reactors, continuous flow fixed bed reactors, slurry reactors, fluidized bed reactors, and catalytic distillation reactors. The form of the bimetallic ruthenium-ligand complex component, may influence the choice of reactor. For example, if the bimetallic ruthenium-ligand complex component is provided homogeneously (solubilized in one or more reactants or solvent), then a batch reactor may be preferable. If the bimetallic ruthenium-ligand complex component is provided in heterogeneous form (deposited or bonded onto a solid support), then a continuous flow fixed bed reactor, fluidized bed reactor, or catalytic distillation reactor may be preferable.

The olefin metathesis process of this invention can be conducted under any operable process conditions of temperature, pressure, and liquid and gas flow rates. The process temperature is advantageously greater than about 85° C., preferably, greater than about 95° C., more preferably, greater than about 100° C., and most preferably, greater than about 110° C. The process temperature is advantageously less than about 200° C., preferably, less than about 180° C., and more preferably, less than about 170° C. When using a gaseous olefinically-unsaturated reactant, the olefin pressure is advantageously greater than about 0 psig (0 kPa gauge), preferably, greater than about 10 psig (68.9 kPa), and more preferably, greater than about 45 psig (310 kPa). Advantageously, the pressure of the olefinically-unsaturated reactant is less than about 700 psig (4,826 kPa), and more preferably, less than about 500 psig (2,758 kPa). When a gaseous diluent is used with the olefinically-unsaturated reactant, the aforementioned pressure ranges may be advantageously employed as the total pressure of olefin and diluent. Likewise, when the olefinic reactant(s) is(are) not in a gaseous phase, and the process is conducted under an inert gaseous atmosphere, the inert gas pressure is advantageously greater than about 0 psig (0 kPa gauge), preferably, greater than about 10 psig (68.9 kPa), and more preferably, greater than about 45 psig (310 kPa), and advantageously, less than about 700 psig (4,826 kPa), and more preferably, less than about 500 psig (2,758 kPa).

The quantity of bimetallic ruthenium-ligand complex that is employed is any quantity that provides for an operable olefin metathesis process. If the process is conducted in batch, the ratio of moles of olefinically-unsaturated reactant to moles of bimetallic ruthenium-ligand complex is advantageously greater than about 10:1, preferably, greater than about 50:1, and more preferably, greater than about 100:1. Under batch conditions, the molar ratio of olefinically-unsaturated reactant to bimetallic ruthenium-ligand complex advantageously does not exceed about 1,000, 000:1, but preferably, is less than about 500,000:1, and more preferably, is less than about 200,000:1. The contacting time of the olefinic reactants and catalyst system in a batch reactor can be any duration, provided that the desired metathesis products are obtained. The contacting time in a batch reactor is advantageously greater than about 30 minutes, and preferably, greater than about 1 hour. The contacting time in a batch reactor is advantageously less than about 25 hours, preferably, less than about 15 hours, and more preferably, less than about 10 hours.

When the process is conduced in a continuous flow reactor, then weight hourly space velocity, given in units of grams olefinically-unsaturated reactant per gram bimetallic ruthenium-ligand complex per hour ($h^{-1}$), determines the relative quantities of olefinic reactant and catalyst employed as well as residence time in the reactor of the olefinic reactant. In a flow reactor, the weight hourly space velocity (WHSV) of the olefinically-unsaturated reactant is advantageously greater than about 0.04, and preferably, greater than about 0.1 g reactant per g bimetallic ruthenium-ligand complex per hour ($h^{-1}$). In a flow reactor, the WHSV of the olefinically-unsaturated reactant is advantageously less than about 100 $h^-$, and preferably, less than about 20 $h^{-1}$.

Numbered Embodiments of the Invention Include

1. An olefin metathesis process comprising contacting one or more olefinically-unsaturated reactants with a metathesis catalyst system under reaction conditions sufficient to prepare one or more olefinically-unsaturated products that are different from the olefinically-unsaturated reactant(s); the catalyst system comprising a carbene-generating agent, a bimetallic ruthenium-ligand complex represented by Formula I hereinafter:

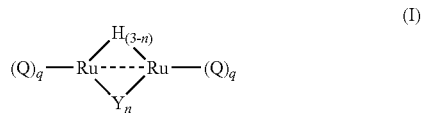

(I)

wherein each q is 1; each Q is independently selected from 6-electron donor arene ligands; wherein each n is the same and is 0, 1, or 2; wherein each Y is an anionic di(t-butyl) phosphido ligand, with the proviso that when n=0, then the catalyst system further comprises di(tertiary-butyl)phosphine.

2. Embodiment 1 wherein the metathesis comprises ring-opening metathesis polymerization comprising contacting an olefinically-unsaturated cyclic compound having at least one internal carbon-carbon double bond with the aforementioned catalyst system, the contacting being conducted under reaction conditions sufficient to prepare an olefinically-unsaturated polymer.

3. Embodiment 1 wherein the olefin metathesis process comprises ring-closing metathesis comprising contacting an olefinically-unsaturated acyclic diene with the aforementioned catalyst system, the contacting being conducted under reaction conditions sufficient to prepare an olefinically-unsaturated cyclic compound.

4. Embodiment 1 wherein the olefin metathesis process comprises ethenolysis of an olefinically-unsaturated fatty acid or olefinically-unsaturated fatty acid ester, the process comprising contacting said olefinically-unsaturated fatty acid or ester with ethylene in the presence of the aforementioned catalyst system, the contacting occurring under process conditions sufficient to prepare a reduced-chain olefinically-unsaturated acid or ester.

5. Embodiment 1 wherein the olefin metathesis process comprises polymer segment interchange olefin metathesis process comprising contacting an olefinically-unsaturated polymer or a mixture of olefinically-unsaturated polymers, optionally in the presence of ethylene, in the presence of the aforementioned catalyst system, the contacting being conducted under reaction conditions sufficient to prepare an olefinically-unsaturated polymer product composition different from the reactant polymer(s).

6. Any of the aforementioned embodiments as applicable wherein the olefinically-unsaturated reactant comprises an acyclic C2-C30 olefinic hydrocarbon, preferably, an acyclic C2-C-20 olefinic hydrocarbon, more preferably, an acyclic C2-C10 olefinic hydrocarbon, including terminal and internal isomers thereof.

7. Any of the aforementioned embodiments as applicable wherein the olefinically-unsaturated reactant is selected from propylene, butene, butadiene, pentene, hexene, hexadiene, heptene, octene, octadiene, nonene, decene, dodecene, and higher homologues thereof, including both terminal and internal unsaturated isomers thereof, as well as acid, ester, aldehyde, and hydroxy substituted variants thereof, as well as diethyl diallyl malonate, and mono-, di-, and tri-unsaturated fatty acids and fatty acid esters having from about 6 to about 30 carbon atoms per fatty acid chain, preferably as unsaturated fatty acid esters, the glyceride esters, the esters of pentaerythritol, and the esters of C1-C10 mono-alkanols, more preferably, oleic acid and C1-C5 alkyl oleate.

8. Any one of the aforementioned embodiments as applicable wherein the olefinically-unsaturated reactant comprises monocyclic or polycyclic olefin advantageously comprising about C4-C25 carbon atoms, preferably, C4-C12 carbon atoms, and more preferably, C4-C10 carbon atoms.

9. Any one of the aforementioned embodiments as applicable wherein the olefinically-unsaturated reactant is selected from cyclopentene, cyclopentadiene, cyclohexene, cyclohexadiene, cycloheptene, cyclooctene, cyclooctadiene, 2-ethylcyclohexene, and 2-ethylcyclohexadiene.

10. Any one of the aforementioned embodiments as applicable wherein the olefinically-unsaturated reactant is selected from olefinically-unsaturated polymers having a molecular weight of at least 500, preferably at least 1000, and less than 1,000,000.

11. Any one of the aforementioned embodiments as applicable wherein two olefinically-unsaturated compounds are employed in the process, and the relative quantities of either one to the other advantageously range from about 0.5/1 to about 2/1 on a molar basis, and preferably, from about 0.8/1 to about 1.3/1, and more preferably, from about 0.9/1 to about 1.1/1.

12. Any one of the aforementioned embodiments wherein a solvent is employed selected from aromatic hydrocarbons, preferably, benzene, toluene, and xylenes; chlorinated aromatic hydrocarbons, preferably chlorinated benzenes, such as chlorobenzene and dichlorobenzene; alkanes, preferably, pentane, hexane, heptane, cyclopentane, and methylcyclohexane; and chlorinated alkanes, preferably, methylene dichloride, chloroform, and carbon tetrachloride.

13. Any one of the aforementioned embodiments wherein a solvent is employed such that the concentration of at least one olefinically-unsaturated reactant in the solvent is advantageously greater than about 0.05 M, preferably, greater than about 0.5 M, but advantageously less than about the saturation concentration, preferably, less than about 5.0 M.

14. Any one of the aforementioned embodiments wherein the process is conducted under an inert atmosphere, preferably, helium, neon, argon, nitrogen, and mixtures thereof.

15. Any one of the aforementioned embodiments wherein if any olefinically-unsaturated reactant is provided to the olefin metathesis process as a gas, then that gaseous reactant may be fed to the reactor as an essentially pure gaseous stream or in a stream diluted with a gaseous diluent, preferably, helium, neon, argon, nitrogen, and mixtures thereof.

16. The aforementioned embodiment wherein the concentration of gaseous olefinically-unsaturated reactant in the gaseous diluent is advantageously greater than about 5 mole percent, and preferably, greater than about 10 mole percent olefinic reactant, and advantageously less than 90 mole percent, based on total moles olefinic reactant and gaseous diluent.

17. Any of the aforementioned embodiments wherein the carbene-generating agent is represented by the following Formula II:

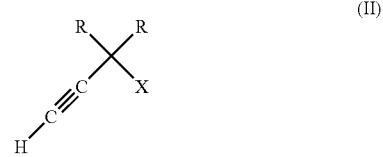

wherein each R is independently selected from hydrogen and monovalent C1-C20 hydrocarbyl groups and substituted variants thereof, preferably, hydrogen, C1-C5 alkyl, and C6-C10 aryl groups; or alternatively, wherein both R groups are bonded together to form a divalent C3-C8 alkylene or divalent C4-C7 arylene group, or substituted variant thereof; and wherein X is either hydroxyl (OH) or halogen, preferably, chlorine.

18. Any of the aforementioned embodiments wherein the carbene-generating agent is selected from 3-chloro-3-methyl-1-butyne, 2-methyl-3-butyn-2-ol, and 1-ethynyl-1-cyclohexanol.

19. Any of the aforementioned embodiments wherein the carbene-generating agent is advantageously added to the catalyst system in a molar ratio greater than about 0.8/1, and preferably greater than about 0.9/1, relative to the bimetallic ruthenium-ligand complex, and advantageously less than about 2.0/1, more preferably, less than about 1.5/1, relative to the bimetallic ruthenium-ligand complex; most preferably, 1.0/1.0.

20. Any one of the aforementioned embodiments wherein the bimetallic ruthenium-ligand complex comprises a monovalent anion, preferably, hexafluorophosphate $(PF_6)^-$, tetraphenylborate $(B\Phi_4)^-$, tetrafluoroborate $(BF_4)^-$.

21. Any of the aforementioned embodiments wherein if di(t-butyl)phosphine is present, then the molar ratio of di(t-butyl)phosphine to bimetallic ruthenium-ligand complex is advantageously greater than about 0.7/1, preferably, greater than about 0.9/1, and advantageously, less than about 3.0/1, and preferably, less than about 2.0/1.

22. Any of the aforementioned embodiments wherein each Q is independently selected from benzene and C1-C20-substituted benzenes, preferably 1,3,5-trimethylbenzene, 1,3,5-diethylbenzene, 1,3,5-tri-isopropylbenzene, 1,3,5-propylbenzene, 1-methyl-4-isopropylbenzene, 1-ethyl-4-isopropylbenzene, 1,2,3,4,5,6-hexamethylbenzene, 1,2,3,4,5,6-hexaethylbenzene, 1,2,3,4,5,6-hexapropylbenzene, and 1,2,3,4,5,6-hexa-isopropylbenzene.

23. Any of the aforementioned embodiments wherein the bimetallic ruthenium complex is selected from:

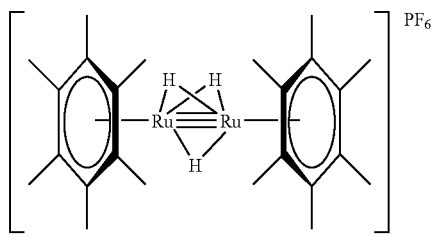

Complex A

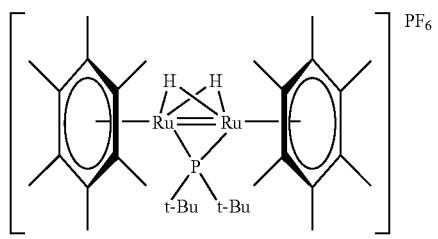

Complex B

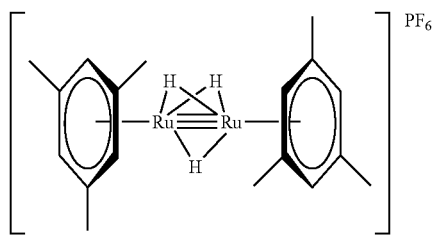

Complex C

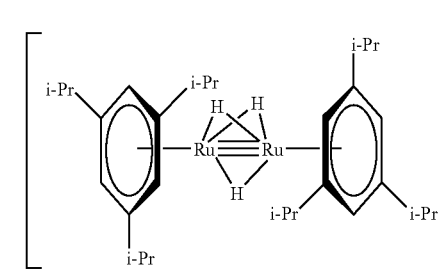

Complex D

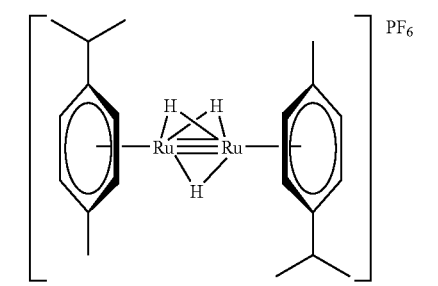

Complex E

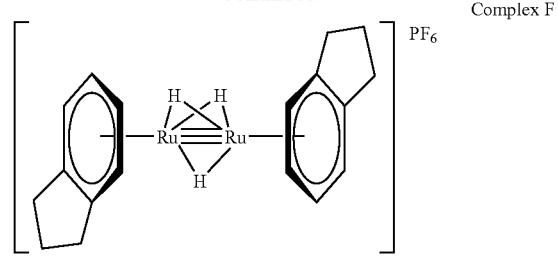

Complex F wherein the hexafluorophosphate anion can be replaced with an equivalent monovalent anion.

24. Any of the aforementioned embodiments wherein the bimetallic ruthenium-ligand complex is bound to or deposited on a solid support selected from silicas, aluminas, silica-aluminas, aluminosilicates, including zeolites and other crystalline porous aluminosilicates; as well as titanias, zirconia, magnesium oxide, carbon, and cross-linked, reticular polymeric resins, such as functionalized cross-linked polystyrenes, e.g., chloromethyl-functionalized cross-linked polystyrenes.

25. The aforementioned embodiment 24 wherein the bimetallic ruthenium-ligand complex is advantageously loaded onto the support in an amount greater than about 0.01, and preferably, greater than about 0.05, and advantageously less than about 20, and preferably, less than about 10 weight percent ruthenium, based on the total weight of the complex and support.

26. Any one of the aforementioned embodiments wherein the olefin metathesis process is conducted in a reactor selected from batch reactors, continuous stirred tank reactors, continuous flow fixed bed reactors, slurry reactors, fluidized bed reactors, and catalytic distillation reactors.

27. Any one of the aforementioned embodiments wherein the process temperature is advantageously greater than about 85° C., preferably, greater than about 95° C., more preferably, greater than about 100° C., and most preferably, greater than about 110° C.; but less than about 200° C., preferably, less than about 180° C., and more preferably, less than about 170° C.

28. Any one of the aforementioned embodiments wherein when using a gaseous olefinically-unsaturated reactant, the olefin pressure is advantageously greater than about 0 psig (0 kPa gauge), preferably, greater than about 10 psig (68.9 kPa), and more preferably, greater than about 45 psig (310 kPa); but less than about 700 psig (4,826 kPa), and more preferably, less than about 500 psig (2,758 kPa).

29. Any one of the aforementioned embodiments wherein when the olefinic reactant(s) is(are) not in a gaseous phase, and the process is conducted under an inert gaseous atmosphere, then the inert gas pressure is advantageously greater than about 0 psig (0 kPa gauge), preferably, greater than about 10 psig (68.9 kPa), and more preferably, greater than about 45 psig (310 kPa), and advantageously, less than about 700 psig (4,826 kPa), and more preferably, less than about 500 psig (2,758 kPa).

30. Any one of the aforementioned embodiments wherein the process is conducted in batch, and the ratio of moles of olefinically-unsaturated reactant to moles of bimetallic ruthenium-ligand complex is advantageously greater than about 10:1, preferably, greater than about 50:1, and more preferably, greater than about 100:1, but does not exceed about 1,000,000:1, but preferably, is less than about 500,000:1, and more preferably, is less than about 200,000:1.

31. Any one of the aforementioned embodiments wherein the contacting time of the olefinic reactants and catalyst system in a batch reactor is greater than about 30 minutes, and preferably, greater than about 1 hour; but less than about 25 hours, preferably, less than about 15 hours, and more preferably, less than about 10 hours.

32. Any one of the aforementioned embodiments wherein the process is conducted in a continuous flow reactor, and the weight hourly space velocity (WHSV) of the olefinically-unsaturated reactant is advantageously greater than about 0.04 gram reactant per gram bimetallic ruthenium-ligand complex per hour ($h^{-1}$) 0, and preferably, greater than about 0.1 $h^{-1}$, and is advantageously less than about 100 $h^{-1}$, and preferably, less than about 20 $h^{-1}$.

33. A metathesis catalyst system comprising a carbene-generating agent and a bimetallic ruthenium-ligand complex represented by the formula:

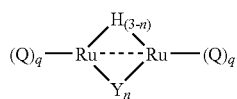

wherein each q is 1; each Q is independently selected from 6-electron donor arene ligands; wherein each n is the same and is 0, 1, or 2; wherein each Y is an anionic di(t-butyl) phosphido ligand, with the proviso that when n=0, then the catalyst system further comprises di(tertiary-butyl)phosphine.

34. The metathesis catalyst system of Embodiment 33 wherein the carbene-generating agent is represented by the following formula:

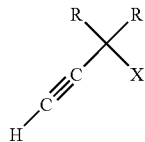

wherein each R is independently selected from hydrogen and monovalent C1-C20 hydrocarbyl groups and substituted variants thereof; or alternatively, wherein both R groups are bonded together to form a divalent C3-C8 alkylene or divalent C4-C7 arylene group, or substituted variant thereof; and wherein X is either hydroxyl or halogen.

The following examples are set forth to illustrate the invention; but these examples should not be limiting thereof. Based on the description herein, the skilled person will be able to substitute different olefinic reactants, different carbene-generating agents, different bimetallic ruthenium-ligand complexes, and a variety of different process conditions for those illustrated in the examples.

All manipulations of air-sensitive materials are carried out in a nitrogen atmosphere glove box. 1,7-Octadiene, diethyl diallyl malonate (DEDAM), cyclooctene, tetrachloroethane, chlorobenzene, and 3-chloro-3-methyl-1-butyne are obtained commercially, then deoxygenated using nitrogen sparging, and purified by passing each sample through a column of activated alumina while in a glovebox under nitrogen. 3-Chloro-3-methyl-1-butyne is stored in a freezer in a glovebox under an inert atmosphere.

All examples and comparative experiments at a given temperature are conducted simultaneously in parallel fashion using similar reagent feedstocks. In the examples and comparative experiments conducted at 80° C. and 100° C., a heated stirring block located in a nitrogen-purged glovebox is used. At reaction temperatures of 120° C. and 140° C., a heated aluminum block located in a nitrogen-purged glovebox is used. At operating temperatures of 120° C. and 140° C. the cyclooctene solutions are pre-heated to the operating temperature prior to addition of the catalyst components in order to account for a longer time for the reaction mixture to reach temperature.

Determine polymer molecular weight using method ASTM D6474-99 (2006): Standard Test Method for Determining Molecular Weight Distribution and Molecular Weight Averages of Polyolefins by High Temperature Gel Permeation Chromatography.

Examples 1(a-d)

Ring Opening Metathesis Polymerization

Four parallel reactions are conducted at 80° C., 100° C., 120° C., and 140° C. in the following manner. A solution of bimetallic ruthenium complex B in tetrachloroethane (0.76 mL of 0.014 M) is mixed with 3-chloro-3-methyl-1-butyne in toluene (0.26 mL of 0.042 M solution). A solution of cyclooctene in toluene (1.40 mL of 0.76 M solution) is added to the solution containing the complex bringing the total volume to 2.94 mL. The reactor is capped and heated to the desired reaction temperature for 3 hours with stirring. At reaction temperatures of 120° C. and 140° C., the solution containing the bimetallic ruthenium complex is added to a preheated solution of cyclooctene in toluene via syringe addition through a septum. At the completion of each reaction, the reactor is cooled to room temperature and quenched with ethyl vinyl ether. Volatiles are removed under vacuum. A yield of polymer product is calculated from the nonvolatile residue remaining in each reactor. Results are shown in Table 1.

TABLE 1

Ring-Opening Metathesis Polymerization

| Ex. | Ru Complex | Carbene-Generating Agent[a] | (t-Bu)$_2$PH | Olefin | Olefin:Ru Complex (mole ratio) | Yield of Polymer (wt %) | | | |
|---|---|---|---|---|---|---|---|---|---|
| | | | | | | (a) 80° C. | (b) 100° C. | (c) 120° C.[b] | (d) 140° C.[b] |
| CE-1 | Grubbs 1 | — | — | Cyclooctene | 500 | 92.8 | 61.5 | 20.7 | 18.1 |
| 1 | B | C$_5$H$_7$Cl | None | Cyclooctene | 500 | 4.2 | 11.2 | 25.2 | 22.5 |

TABLE 1-continued

Ring-Opening Metathesis Polymerization

| Ex. | Ru Complex | Carbene-Generating Agent[a] | (t-Bu)$_2$PH | Olefin | Complex (mole ratio) | Yield of Polymer (wt %) (a) 80° C. | (b) 100° C. | (c) 120° C.[b] | (d) 140° C.[b] |
|---|---|---|---|---|---|---|---|---|---|
| 2 | E | C$_5$H$_7$Cl | Yes | Cyclooctene | 500 | 0.8 | 1.7 | 4.7 | 5.7 |
| CE-2 | Grubbs 1 | — | — | Cyclooctene | 1,000 | 61.6 | 29.0 | 14.5 | 8.4 |
| 3 | B | C$_5$H$_7$Cl | None | Cyclooctene | 1,000 | 1.7 | 5.3 | 20.7 | 16.1 |
| 4 | E | C$_5$H$_7$Cl | Yes | Cyclooctene | 1,000 | 1.1 | 1.4 | 4.2 | 4.1 |

[a]C$_5$H$_7$Cl = 3-chloro-3-methyl-1-butyne
[b]Due to the longer time to reach reaction temperature, the solutions were pre-heated to the reaction temperature prior to the addition of the Ru complex and co-catalytic components.

Examples 2(a-d)

Ring-Opening Metathesis Polymerization

Four parallel reactions are conducted at 80° C., 100° C., 120° C., and 140° C. in the following manner. A solution of bimetallic ruthenium complex E in tetrachloroethane (0.76 mL of 0.014 M) is mixed with 0.26 mL of 0.042 M di-t-butylphosphine (ligand) solution in toluene and 0.26 mL of additional tetrachloroethane for a mole ratio of 1 mole ligand: Ru$_2$. 3-Chloro-3-methyl-1-butyne in toluene (0.26 mL of 0.042 M solution) is added to the solution. A solution of cyclooctene in toluene (1.40 mL of 0.76 M solution) is added to the mixture bringing the total volume to 2.94 mL. The reactor is capped and heated to the desired reaction temperature for 3 hours with stirring. At reaction temperatures of 120° C. and 140° C., the solution containing the bimetallic ruthenium complex is added to a preheated solution of cyclooctene in toluene via syringe addition through a septum. Following the reaction period the reactor is cooled to room temperature, and the reaction mixture is quenched with ethyl vinyl ether. Volatiles are removed from the samples under vacuum. A yield of polymer product is calculated from the nonvolatile residue remaining in each reactor. Results are shown in Table 1.

Comparative Experiments 1(a-d)

The procedure of Examples 1 and 2 is repeated with the exception that a monatomic Ru Grubbs I metathesis catalyst, namely, benzylidene-bis(tricyclohexyl-phosphine)dichlororuthenium (0.76 mL of 0.014 M) replaces the catalyst system of ruthenium complex B in Example 1 and the catalyst system comprising ruthenium complex E and carbene generating agent in Example 2. Results are shown in Table 1.

As seen in Table 1, at a 500:1 molar ratio of olefin reactant: Ru complex, the prior art catalyst of Comparative Experiments CE-1(a-d) exhibits a decrease in the yield of polymer product with an increase in process temperature. Conversely, the catalyst systems derived from the bimetallic complexes B (Examples 1a-d) and E (Examples 2a-d) exhibit an increase in activity and polymer product yield with increasing temperature. In going from 120° C. through 140° C. some leveling off occurs in polymer yield; but the catalyst systems based upon complex B and complex E are more active than the prior art catalyst under similar process conditions.

Examples 3(a-d)

Ring-Opening Metathesis Polymerization

Examples 1(a-d) are repeated with the exception that the quantity of bimetallic ruthenium complex B is reduced by 50% in each run resulting in a molar ratio of olefin reactant to bimetallic ruthenium complex of 1000:1. Results of the metathesis evaluation are shown in Table 1.

Example 4(a-d)

Ring-Opening Metathesis Polymerization

Examples 2(a-d) are repeated with the exception that the quantity of bimetallic ruthenium complex E is reduced by 50% in each run resulting in a molar ratio of olefin reactant to bimetallic ruthenium complex of 1000:1. Results of the metathesis evaluation are shown in Table 1.

Comparative Experiment CE-2(a-d)

Comparative Experiments CE-1(a-d) are repeated with the exception that the quantity of Grubbs I catalyst is reduced by 50% in each run resulting in a molar ratio of olefin reactant to Grubbs I complex of 1000:1. Results of the metathesis evaluation are shown in Table 1.

As seen in Table 1, at a 1000:1 molar ratio of olefin reactant:Ru complex, the prior art catalyst of Comparative Experiments CE-2(a-d) exhibit a decrease in the yield of polymer product with an increase in process temperature. Conversely, the process of the invention as illustrated in Examples 3(a-d) and 4(a-d), using ruthenium complexes B and E, respectively, exhibits an increase in activity and polymer product yield with increasing temperature. In going from 120° C. through 140° C. some leveling off occurs in polymer yield; but the systems based upon Ru complex B and E are more active than the prior art catalyst under similar process conditions.

Examples 5 to 29

Ring-Closing Metathesis

The following general procedure is employed to evaluate several catalysts in (a) the catalytic metathesis cyclization of 1,7-cyclooctadiene to cyclohexene, or (b) the catalytic metathesis cyclization of diethyl diallyl malonate to 3-cyclopentene-1,1-dicarboxylic acid, 1,1-diethyl ester. The procedure involves adding a solution of the selected Ru complex (0.760 mL of 0.014 M solution in chlorobenzene, 0.01064 mmol) to a reactor followed by addition of the carbene-generating agent (0.260 mL of 0.042 M solution in toluene, 0.01064 mmol). In certain examples, di(t-butyl)phosphine (Ligand) is added to the reaction mixture in a Ligand/Ru$_2$ molar ratio as shown. To the resulting mixture is added the diene (1.4 mL of 0.76 M solution of 1,7-octadiene or diethyl diallyl malonate in toluene, 1.064 mmol). The reactor vial is capped and heated with stirring to reaction temperature for a designated reaction time. After the reaction period, the reaction mixture is cooled to room temperature, quenched with ethyl vinyl ether, and then analyzed using gas chromatographic (GC) analysis. Results are shown in Table 2.

TABLE 2

| | | Cyclization Metathesis | | | | | | |
|---|---|---|---|---|---|---|---|---|
| Ex. | Ru$_2$ Complex | (tBu)$_2$PH (L) Y = yes N = no | L:Ru$_2$ Mole Ratio | Carbene Source | T (°C.) | Time (h) | Olefin (OL) | OL:Ru$_2$ | Conv. (%) |
| 5 | A | Y | 1 | 3-chloro-3-methyl-1-butyne | 80 | 3 | 1,7-octadiene | 100 | 29.5 |
| 6 | A | Y | 2 | 3-chloro-3-methyl-1-butyne | 80 | 3 | 1,7-octadiene | 100 | 20.9 |
| 7 | A | Y | 1 | 3-chloro-3-methyl-1-butyne | 80 | 3 | diethyl diallyl malonate | 100 | 5.0 |
| 8 | A | Y | 2 | 3-chloro-3-methyl-1-butyne | 80 | 3 | diethyl diallyl malonate | 100 | 2.4 |
| 9 | B | N | NA | 3-chloro-3-methyl-1-butyne | 80 | 3 | 1,7-octadiene | 100 | 47.8 |
| 10 | B | N | NA | 3-chloro-3-methyl-1-butyne | 80 | 3 | Diethyl diallyl malonate | 100 | 12.1 |
| 11 | C | Y | 1 | 3-chloro-3-methyl-1-butyne | 80 | 3 | 1,7-octadiene | 100 | 79.4 |
| 12 | C | Y | 1 | 3-chloro-3-methyl-1-butyne | 80 | 3 | diethyl diallyl malonate | 100 | 29.9 |
| 13 | D | Y | 1 | 3-chloro-3-methyl-1-butyne | 80 | 3 | 1,7-octadiene | 100 | 21.2 |
| 14 | D | Y | 1 | 3-chloro-3-methyl-1-butyne | 80 | 3 | diethyl diallyl malonate | 100 | 8.3 |
| 15 | E | Y | 1 | 3-chloro-3-methyl-1-butyne | 80 | 3 | 1,7-octadiene | 100 | 98.7 |
| 16 | E | Y | 2 | 3-chloro-3-methyl-1-butyne | 80 | 3 | 1,7-octadiene | 100 | 77.9 |
| 17 | E | Y | 1 | 1-ethynyl-1-cyclohexanol | 80 | 3 | 1,7-octadiene | 100 | 25.7 |
| 18 | E | Y | 1 | 2-methyl-3-butyn-2-ol | 80 | 3 | 1,7-octadiene | 100 | 45.3 |
| 19 | E | Y | 1 | 3-chloro-3-methyl-1-butyne | 80 | 3 | diethyl diallyl malonate | 100 | 79.2 |
| 20 | E | Y | 1 | 1-ethynyl-1-cyclohexanol | 80 | 3 | diethyl diallyl malonate | 100 | 11.6 |
| 21 | E | Y | 1 | 2-methyl-3-butyn-2-ol | 80 | 3 | diethyl diallyl malonate | 100 | 20.9 |
| 22 | E | Y | 2 | 3-chloro-3-methyl-1-butyne | 80 | 3 | diethyl diallyl malonate | 100 | 50.1 |
| 23 | E | Y | 1 | 3-chloro-3-methyl-1-butyne | 60 | 24 | 1,7-octadiene | 1000 | 43.5 |
| 24 | E | Y | 1 | 3-chloro-3-methyl-1-butyne | 80 | 24 | 1,7-octadiene | 1000 | 71.2 |
| 25 | E | Y | 1 | 3-chloro-3-methyl-1-butyne | 100 | 7 | 1,7-octadiene | 1000 | 68.0 |
| 26 | E | Y | 1 | 3-chloro-3-methyl-1-butyne | 60 | 24 | diethyl diallyl malonate | 1000 | 6.0 |
| 27 | E | Y | 1 | 3-chloro-3-methyl-1-butyne | 80 | 24 | diethyl diallyl malonate | 1000 | 20.1 |
| 28 | E | Y | 1 | 3-chloro-3-methyl-1-butyne | 100 | 24 | diethyl diallyl malonate | 1000 | 25.5 |
| 29 | F | Y | 1 | 3-chloro-3-methyl-1-butyne | 80 | 3 | 1,7-octadiene | 100 | 30.9 |

What is claimed is:

1. A metathesis catalyst system comprising a bimetallic ruthenium-ligand complex represented by the following formula:

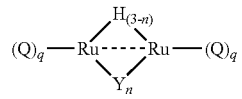

wherein each q is 1; each Q is independently selected from 6-electron donor arene ligands; wherein each n is the same and is 0, 1, or 2; wherein each Y is an anionic di(t-butyl)phosphido ligand, with the proviso that when n=0, then the catalyst system further comprises di(tertiary-butyl)phosphine and a carbene-generating agent that is represented by the following formula:

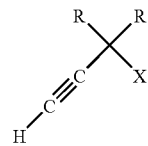

wherein each R is independently selected from hydrogen and monovalent C1-C20 hydrocarbyl groups and substituted variants thereof; or alternatively, wherein both R groups are bonded together to form a divalent $C_3$-$C_8$ alkylene or divalent $C_4$-$C_7$ arylene group, or substituted variant thereof; and wherein X is either hydroxyl or halogen.

* * * * *